United States Patent [19]

Hodges et al.

[11] Patent Number: 5,677,175

[45] Date of Patent: Oct. 14, 1997

[54] PLANT PATHOGEN INDUCED PROTEINS

[75] Inventors: Thomas K. Hodges, West Lafayette, Ind.; J. David McGee, Manhatten, Kans.

[73] Assignee: Purdue Research Foundation, West Lafayette, Ind.

[21] Appl. No.: 728,956

[22] Filed: Oct. 11, 1996

Related U.S. Application Data

[63] Continuation-in-part of Ser. No. 5,362, Oct. 13, 1995, abandoned.

[51] Int. Cl.⁶ .............................. C12N 15/70; C12N 5/10

[52] U.S. Cl. .................. 435/320.1; 435/69.1; 435/172.3; 435/410; 435/419; 800/200; 800/205; 800/250

[58] Field of Search ........................ 435/69.1, 320.1, 435/810, 172.3, 410, 419; 436/501; 800/205, 200, 250; 935/77, 78

Primary Examiner—Ardin H. Marschel
Attorney, Agent, or Firm—Barnes & Thornburg

[57] ABSTRACT

The present invention is directed to DNA constructs comprising a pathogen inducible promoter operably linked to a disease resistance gene, and the use of those DNA constructs to produce transgenic disease resistant plants.

7 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2593 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oryza sativa ( x i ) SEQUENCE DESCRIPTION: SEQ ID NO:1:

```
CCGTCGTTCG  TTCGCGGTCG  GGCTCCTTGA  CACCGTCGCA  GACGGCCGCC  CGTGGCGCTC     60

AGGGTGCATG  GTTGCAACCA  TTTTGGCGCC  TACTTCTCGC  GGAGGCCGGC  GAGGTGCACG    120

CTCGATGGGG  CCGACATGGG  GTTCACCTAC  TACGGCGACA  CGAGGACATG  CTCACAGAGG    180
```

-continued

| | | | | | |
|---|---|---|---|---|---|
| GACCCGCGTC | GGATTAATTT | GAGCCAAGGG | AAAACTGGTC | TTTAATGATT | ATTTCTCTCT | 240 |
| CCTATTTCTC | TAAAAATAAT | AAAATAATCT | CACCGGTGTC | CAGCAGCTAA | TTAACAGTTT | 300 |
| TTTGTGATGC | CCTACAGCAA | ATACACGTTC | TTACGACATC | CCCTAGCTAA | TTACACGTTT | 360 |
| TTCGGACGTC | CTGTAGCAAA | TTTGCCGTAT | AACAATTACA | TTACTATCCT | CATCTTTCCA | 420 |
| AACCAAGGGT | AGGAAGTAGA | GAACTTCTCT | AAAAGTGTTT | TGGAATGTAA | GAACATATTT | 480 |
| TGACACAAGT | TTTGAATGCT | GGAATGATAA | GCAATTTGAA | ACGGAGAGAT | TTATCAAAGT | 540 |
| TAGGACGTAC | GTGCTCTGGT | ACTAGCCGTA | CGATGACGCC | CAATAATTCA | ACCGAAGAAC | 600 |
| AACCACACCT | ATCGATCCGA | GGTGGCAAGG | TGGAAATTTT | GCGTTAAAGC | TCAATTTGTC | 660 |
| CCTGGTGACC | GTGACATCAG | ATTGAGTATC | ACTGAGTCTA | CCAATTGAAG | GTTGTATATA | 720 |
| TCCGAGGTGG | CACAGTGAAA | ATTGATACGC | TATGAAACCC | AACAAGATTG | AAAGAAATTC | 780 |
| ATAATTGAAT | TAATACCTAC | CGATAAAGGG | TATTTGTTTA | GACCCATCTC | AGAGCATGAC | 840 |
| ATGTAGTCGT | ACCTATCATC | TAAAAGCATT | TAAATTAGGG | TCTGTTCGAT | TTAGATTATT | 900 |
| AAACAAATTA | TTATCGTTGA | TTACCTACCA | ATTGATTATG | GAAATAAATT | AAATACTTTA | 960 |
| AAATTAAACT | TAATAAATAG | TTTAAAACAA | GTGATCAAAG | CAGTAGAATA | AAGTTTGTTG | 1020 |
| AGAGATTTTT | TGAAACATAG | AACAAATAAT | CAGTTCCAAT | AATCCGGCGA | ATAATCTGAG | 1080 |
| AATCAGTGTT | CTAACTGTAA | ACAAGACCA | TGATCTCATA | TATGATTATT | CTCCCAACCG | 1140 |
| TCCTATATAT | GCCCAGGTCT | CAAATGTCAG | CTCTTCTAGA | TGGAACCAAA | GAAAAAAACC | 1200 |
| CTTAATTTCC | ACAGGTCAAG | CCACATGTGA | TCCCAATAT | TCCTACTTCC | AGAACCCTAG | 1260 |
| AATTCCACAC | AAAGTTCAGA | TATGCAACCA | ATGGAGCTGA | GTTCCCAACT | GCAACATTTA | 1320 |
| TTCTGGATGA | TGTCTTCTTC | TCCTCTTGCC | ACCCTATAAA | TAGCCCATGC | TACTGCTCAC | 1380 |
| CTTTGAAGCA | CAAGCACAAG | CACAAGCAGC | TCTAGCTAGC | TACAGGCATC | AGTGGTCAGT | 1440 |
| AGAGTGATCA | GTTGCAACTA | GCTAGCTAGT | TAGATTATAT | CTTCAGTGAT | GGCTCCGGCC | 1500 |
| TGCGTCTCCG | ACGAGCACGC | CGTCGCGGTG | TCGGCGGAGC | GGCTGTGGAA | GGCGTTCATG | 1560 |
| GACGCGTCCG | CTTTGCCCAA | GGCCTGCGCC | GGCTTGGTCG | ACGACATTGC | GGTCGAGGGG | 1620 |
| AACGGCGGTC | CGGGCACCAT | CTACACCATG | AAGCTTAACC | CTGGTAGGTC | CAGAAAGATC | 1680 |
| TAAGTACTTG | TATCTACTGA | TTGTACTTAT | TATCTCGGCC | GATTTTTTT | CTTAAATTTT | 1740 |
| TGTGAATTTG | GTCAAAATTT | AGTCAAATTC | AGTTAAATTA | TTTTCAAATT | TCTGAAAAAA | 1800 |
| AATCGGTCCA | AAAAGTGCCG | AAAATCCCGA | AATTTTGGTT | CTACCAAAAT | GGCCGAAATT | 1860 |
| TTCGGCGAAA | TCGAAAGTGA | AAATCCTGTC | AACAACAAAA | AGAATTTGAT | TAAGACAGTT | 1920 |
| AAAATTACTA | TAGTGCAGTA | TAAAATTGAT | TGGGTATATA | ATAACAACAA | ATGTTAAAAT | 1980 |
| TATATGCAGC | CGCGGGTGTG | GGAAGCACAT | ACAAGACCCG | GGTGGCGGTG | TGCGACGCCG | 2040 |
| CAAGTCATGT | CCTAAAGTCG | GATGTGCTCG | AGGCAGAAAG | CAAGGTGGGG | AAGCTCAAGT | 2100 |
| CACACTCGAC | GGAGACGAAG | CTTCAGGCCA | CCGGCGATGG | CTCCTGCGTG | GCCAAGCTCA | 2160 |
| AGGTGGAGTA | CGAGCTCGAG | GATGGCAGCT | CACTGTCGCC | GGAGAAGGAG | AAGGACATCG | 2220 |
| TGGATGGCTA | CTATGGCATG | CTCAAGATGA | TCGAGGACTA | CCTCGTCGCT | CACCCTGCCG | 2280 |
| AATACGCCTA | AGATGAAGAG | GAATACTGCC | TCTATCCAGT | ATATCCCACC | TAGAGTGAGT | 2340 |
| GATAATTAAA | TAATGAGAGC | CGCAGAAATG | TCCAAATTCT | CGTGGCGTTT | GAGTCCGTGA | 2400 |
| GAGTAATTTC | GTGCTTTAAG | TTTGTGGTTG | TGTTTATGTG | CCTTTCTATG | GTCGTATGCA | 2460 |
| GTGTTAAAGT | TATCATTTTG | CTTCATCAAT | GGGTGAATAA | AGAGAGGCAA | GTCTGAATGT | 2520 |
| GTTCTGCTAT | GGTTTGGAGG | TTAATATGGA | AGATTGAAAA | TCATTGTGAA | TGCTGCCGAT | 2580 |

```
CAGAAATACT ACA                                                                                          2593
```

( 2 ) INFORMATION FOR SEQ ID NO:2:

( i ) SEQUENCE CHARACTERISTICS:
        ( A ) LENGTH: 613 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oryza sativa ( x i ) SEQUENCE DESCRIPTION: SEQ ID NO:2:

```
ACTGCAAGAA  TTTCATGGAC  ATAACCGAAA  TCATCTCAAA  GACCCCTCCA  ACCTTATCTG        60
AGAGAGTCAG  ACATTCTAGT  ACACTGGTCA  AACTCTGAAC  TGATCGATCA  TCTGCATAAA       120
TAAATTGAAA  CACTGAATTT  TCCACAGGTC  AAACCATGTG  ATCTCCATAG  CCCCAGTTTC       180
CTGGTACTAA  AACCCTGAAT  TCCACATATC  AAACTAAACT  ACAAATCAAC  CGGAGAAAAG       240
CCGGATGCGG  TCCTCTTTCA  CCTATAAGTA  TCCCCATTCT  GCAGCTCACC  TTTGAAGCAG       300
AAGAAAAGC   AGCTGAGCTG  AGCTAGCTAT  AGCCATCACA  GCAAGTGTCA  GGTGGAAACT       360
AGCTTAGATA  GAGATGGCTC  CGGCCTTCGT  CTCCGACGAG  CGCGGCGTCG  CGGTGTCGGT       420
GGAGAGGCTG  TGGAAGGTCT  GCTTGGACGT  GCACTCCCTG  CCCAAGGTCT  GCGCCGGAAG       480
CATAAAGTGT  AAAGCCTGGG  GTGCCTAATG  AGTGAGCTAA  CTCACATTAA  TTGCGTTGCG       540
CTCACTGCCC  GCTTTCCAGT  CGGGAAACCT  GTCGTGCCAG  CTGCATTAAT  GAATCGGCCA       600
ACGTGCGGGG  AGA                                                             613
```

( 2 ) INFORMATION FOR SEQ ID NO:3:

( i ) SEQUENCE CHARACTERISTICS:
        ( A ) LENGTH: 1591 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oryza sativa ( x i ) SEQUENCE DESCRIPTION: SEQ ID NO:3:

```
GAGCTCGCCG  TCACGGTGTT  GGCGGAGAGG  CTGTAGAAGG  TGTTCATGGA  CGCGTCCGCC        60
ATGCCCAAGG  TCTGTGCCGG  CTTCGTCGAC  GACATTGTGG  TTGAGGGGAA  TGGCGGTCCA       120
CGCACCATCT  AGCATTGGCA  CATTTTCACT  TCGTACACCT  GTAATTTGG   AAAAGAAATT       180
TTGGGAGGTG  GGGGTGAGGA  GCTTAATTTT  CATCCTTTAG  GCTAAGCTCG  GGAGTGAGGG       240
TTGGGAACCT  TCACTTTCAG  CATGCAAAAT  GAAGCGGCGG  TTAGCGCATG  ACTAATTAAG       300
TTTTAGCTAA  CATAAGCATT  GAAATAGATT  ATTATGATTT  TCTAAACAA   CTTTCATATA       360
GATATTTTTT  TGTAAAAACA  AAATTTAGAA  GTTTGATAAG  CATACCTGCG  AAAAACGAGG       420
TAGAAGTTTG  CAAGGAAAGT  TTAGAACACA  GCCTAGTATT  TTTTTTTTT   TGGATCTTTC       480
```

-continued

| | | | | | |
|---|---|---|---|---|---|
| TACTAACCTA | GCCTCATCTG | TCACTCGGTA | TCTTGAGATA | AGTTGAGATC | TTAACTAAGA | 540
| TAGTGTTTAG | GAAGAAGTGA | CTAAAGTTTA | GTCTCTCACA | CAAAAATTTT | AGTCTCTCCT | 600
| ATAGGGACTT | ATGTTTTGT | GAGAGGGACT | AAAGTTTAGT | CCCTCCTTCC | CAAACACCAC | 660
| CTAATTAAGA | GGGTTAAAAG | GACAGCTGTG | CAAGGCGAAT | TGATTGGGTA | TGTATAACAG | 720
| CAAATACTCC | CTCCGTTTCA | AAATGTTTGA | CACCGCTGAT | TTTTTTTTG | TATATGTTTG | 780
| ATCATTTGTC | TTATTCAAAA | AATTTAAGTA | ATTATTTATT | ATTTTCGTAT | CATTTGACTC | 840
| ATTGTTAAAT | ATACTTTCAT | GTGCACATAT | AGTTTTACAT | ATTTCACAAA | TTTTTTTGAA | 900
| TAAGACGAAC | GGTCAAACAT | GTGCTAAAAA | ATTAAAGGTG | TCAAATATTT | TGAAACGGAG | 960
| GGAGTATTCC | TATATATGCA | GATGCGGGAG | TCGGGAATAC | ATACAAGACC | CGAGTGGCGG | 1020
| TGTGTGACAA | TGCAGCACGC | GTGCTAAAGT | CAGAGGTGCT | GGAGGCAGAA | AGCAAGGTGG | 1080
| GCAAGCTCAA | GTCGCACTCG | ACGGAGACGA | AGCTGGAGGG | CACCGGCGAT | GGCTCCTGCG | 1140
| TGGCCAAGCT | CAAGGTGGAG | TACGAGCTCG | CCGACGGCAG | CTCGCTGACG | CCGGAGCAGG | 1200
| AGAAGACGGC | TACTTCGGCA | TGCTCAAGAT | GATGGAGGCG | TACCTCGCCG | CTCACCCTGC | 1260
| CGAATTCGCC | TGACAAACTG | TCTCAACCAA | CACAATCCAT | GGCTGATAAT | TAAATAATGC | 1320
| GAGCTCCAAT | TTTCTCGTGG | CGTTTGATTT | TTTTGAGAGC | AGTTAATAAT | TTGTGATATT | 1380
| GTGTTGTATG | TGCCTAGCTA | GCTATGTATG | CCGTACGTAC | GAGCATGTAC | TTTTACTTCG | 1440
| ATAATGAATA | AAGAGACAAA | CATCTGAACA | CGTGTTGTGG | TTGAATTTGG | AGGCTAAAAT | 1500
| ATTATTGCAA | CATCAATGCA | ACTAATAGCA | TATATGACAA | AAGGCGACCA | ATAGCATATT | 1560
| AGGTAAGATT | ACAATGACAG | CTAGAAGATT | G | | | 1591

PLANT PATHOGEN INDUCED PROTEINS

This is a continuation-in-part application of U.S. application Ser. No. 60/005,362, filed Oct. 13, 1995, abandoned.

FIELD OF THE INVENTION

The present invention is directed to nucleic acid sequences encoding proteins that are expressed in plant cells in response to the presence of a plant pathogen and DNA constructs comprising those nucleic acid sequences.

BACKGROUND

The protection of plants from disease is a major challenge to farming worldwide. The ability of a plant to recognize the presence of a potential pathogen is central to the plants competency to fight off disease. The cellular process involved in plant disease resistance are poorly understood (except for a few cases), however a resistant plant typically activates a multicomponent system of defense in response to a pathogenic attack. This system of defense can include a transient flux of ions across the plasma membrane, an intracellular oxidative burst, localized cell necrosis and cell death at the site of infection, the synthesis of low molecular weight antimicrobial metabolites (phytoalexins), the formation of polymers which act as physical barriers, the production of a diverse group of pathogen related (PR) proteins which includes hydrolytic enzymes and other antimicrobial compounds, and a systemic signaling through plant phloem to secondary tissues that triggers a long-lived spectrum of pathogenic resistance.

Some plants respond naturally to pathogen attack by activating specific disease-related genes. These genes have been introduced into other plant species, or alternatively the expression of these genes has been enhanced in the originating species, in an attempt to provide higher levels of resistance to pathogens. This approach has achieved the best results using genes encoding the hydrolytic enzymes chitinase and β-1,3-glucanase. These enzymes have been shown in in vitro studies to be active against several fungal pathogens, and in some combinations have been found to act synergistically.

Transgenic plants having introduced chitinase and/or β-1,3-glucanase genes have been produced, and these plants have substantially increased resistance to fungal pathogens. For example, Zhu et al. Bio/Technology 12:807–812 (1994) have reported that tobacco plants containing both a rice RCH10 chitinase gene under the control of the CaMV35S-enhanced promoter and an alfalfa β-1,3-glucanase (AGLU-1) driven by a double CaMV35S promoter exhibit an 88% decrease in lesion size, a 75% reduction in lesion number, and a 3–4 day delay in the appearance of disease symptoms.

Furthermore, Tobacco transformed with DNA sequences encoding either a barley class-II chitinase, a class-II β-1,3-glucanase, or a Type-I ribosome-inactivating protein (RIP), or a combination of those three genes had enhanced resistance to fungal infection. In particular, fungal infection (R. solani) assays revealed that reductions in disease severity were significant for plant lines expressing one of these barley genes (reductions of 51% for RIP; 35% for chitinase, and 53% for glucanase). In addition, the co-expression of either β-1,3-glucanase and chitinase, or chitinase and RIP resulted in a significantly enhanced protection against fungal attack as determined by the percentage reduction in disease severity versus the amount of protein. In all cases, the observed reductions in disease severity by the combined antifungal proteins were at least 1.5- to 2-fold higher than the calculated additive effects of the respective proteins.

Most of the work directed to enhancing disease resistance in plants by introducing PR-genes (genes encoding pathogen related proteins) into the plants cells has utilized the CaMV35S promoter to drive expression of the PR-gene. In dicots this promoter is constitutively expressed at high levels, and this could represent a utilization of metabolic energy that is not necessary to maintain the disease-resistant phenotype of the plant. In at least one report, male sterility was induced by the constitutive expression of β-1,3-glucanase (Worral et al. The Plant Cell 4:759–771, 1992). To circumvent this problem, inducible promoters can be utilized to drive the expression of pathogen resistance genes. In particular, a pathogen-inducible promoter can be operably linked to a pathogen resistance gene so the gene is only expressed when the plant is contacted with the pathogen.

SUMMARY OF THE INVENTION

The present invention is directed to a method of enhancing plant resistance to disease by introducing a DNA construct into the plant cells wherein the DNA construct comprises a pathogen related gene operably linked to a pathogen-inducible promoter. The pathogen resistant plant entities produced in accordance with the present invention express the disease resistance genes only when the plant cells detect the presence of the pathogen. Accordingly, the disease resistant plants of the present invention do not suffer the disadvantages that accompany the constitutive expression of disease resistance genes (i.e. higher metabolic load, male sterility, and other secondary effects).

DETAILED DESCRIPTION OF THE INVENTION

Definitions

A promoter is a DNA sequence that directs the transcription of a structural gene. Typically, a promoter is located in the 5' region of a gene, proximal to the transcription start site of a structural gene. If a promoter is an inducible promoter then the rate of transcription increases in response to an inducing agent. In contrast, the rate of transcription is not regulated by an inducing agent if the promoter is a constitutive promoter.

A pathogen inducible regulatory element is a DNA sequence that directs a higher level of transcription of an associated gene in response to the presence of a pathogen, (as detected by metabolic by-products of the pathogen, pathogen secretions, etc) or in response to damage caused to plant structures either directly or indirectly by the pathogen.

An enhancer is a DNA regulatory element that can increase the efficiency of transcription, regardless of the distance or orientation of the enhancer relative to the start site of transcription.

The term expression refers to the biosynthesis of a gene product. For example, in the case of a structural gene, expression involves the transcription of the structural gene into messenger RNA and the translation of messenger RNA into one or more polypeptides.

An expression vector is a DNA molecule comprising the regulatory elements necessary for expressing an inserted gene in a host cell. Typically gene expression is placed under the control of certain regulatory elements including constitutive or inducible promoters, tissue-specific regulatory elements, and enhancer elements. Such a gene is said to be "operably linked to" the regulatory elements. Expression vectors typically include eukaryotic and/or bacterial selectable markers that allow for selection of cells containing the expression vector.

An exogenous DNA sequence refers to a DNA sequence that has been introduced into a host cell from an external source. A transgenic plant is a plant having one or more plant cells that contain an exogenous DNA sequence. The term stably transformed refers to a transformed cell or plant that is capable of transmitting an exogenous DNA sequence to its progeny. Typically a stably transformed host has the exogenous DNA sequence integrated into its genome.

A core promoter contains the essential nucleotide sequences for promoter function, including the TATA box and start of transcription. By this definition, a core promoter may or may not have detectible activity in the absence of specific sequences that may enhance the activity or confer tissue specific activity.

A visible marker is defined herein as including any gene that encodes a product that produces a phenotypic trait to the host cell or organism.

A selectable marker is defined herein as including any nucleic acid sequence or gene product that can be selected for after introduction into a cell. The selectable marker facilitates the identification of transformants.

A polylinker is a DNA sequence that contains multiple endonuclease restriction enzyme identification sequences in close proximity of one another.

A pathogen related gene is a gene that expresses a product (typically a protein) that enhances the resistance of a plant to a pathogen/disease. Pathogen related (PR) proteins include phytoalexins, hydrolytic enzymes and other antimicrobial compounds.

A plant having "enhanced resistance" refers to a plant that has reduced disease symptoms relative to another plant(i.e. a decrease in lesion size or number) after exposure to a pathogen. Thus a disease-resistant plant is plant having enhanced resistance. The disease-resistant transgenic plants of the present invention have enhanced resistance relative to the original nontransformed plant.

The present invention is directed to disease resistant plants, and a method for producing disease resistant plants through the use of novel DNA constructs. Advantageously the disease resistant plant produced in accordance with the present invention retain their resistance to disease without adding an unnecessary metabolic burden to the plant.

In one embodiment a disease-resistant plant entity is provided wherein the plant entity consists essentially of a plant cell, seed or plant produced from the in vitro introduction of an exogenous nucleic acid sequence into a plant cell. The exogenous nucleic acid sequence comprises a pathogen related gene operably linked to an inducible promoter. The exogenous nucleic acid sequences utilized in accordance with the present invention also typically include a selectable marker gene or a visible marker gene to allow identification of the cells transformed with the exogenous DNA sequence.

In one embodiment an expression vector is provided comprising a pathogen inducible promoter located adjacent to a polylinker region. This expression vector allows the insertion of a preselected gene into the vector so that the gene is operably linked to a pathogen inducible promoter. The expression vector typically includes a selectable marker gene or a visible marker gene to allow identification of plant cells transformed with the exogenous DNA sequence. In one embodiment the expression vector further includes a prokaryotic selectable marker gene and a prokaryotic origin of replication that allows for the transformation and reproduction of the expression vector in prokaryotes.

The pathogen inducible promoter can be selected from the promoter of any plant gene that is induced by the presence of a plant pathogen. In one embodiment the promoter is selected the genes PR-10a (SEQ ID NO: 1), PR-10b(SEQ ID NO: 2) and PR-10c(SEQ ID NO: 3). Alternatively the pathogen regulatory elements of those promoters can be combined with a core promoter not normally associated with the regulatory element to produce new pathogen inducible promoters.

In accordance with the present invention a DNA construct comprising a pathogen-inducible regulatory element selected from the sequences set forth in SEQ ID NO: 1, SEQ ID NO: 2, and SEQ ID NO: 3, a core promoter and a pathogen related gene operably linked to the core promoter is used to transform a plant cell, using procedures known to those familiar with the art. Such transformation procedures include but are not limited to microinjection, mircoprojectile bombardment, electroporation, calcium chloride permeablization, polyethylene glycol permeabilization, protoplast fusion or bacterial mediated mechanisms such as *Agrobacterium tumefaciens* or *Agrobacterium rhizogenes*.

Transformed cells (those containing the DNA inserted into the host cell's DNA) are selected from untransformed cells through the use of a selectable marker included as part of the introduced DNA sequences. Transformed cells/plant entities can also be identified by the expression of a visible marker included as part of the introduced DNA sequences. Visible markers include genes that impart a visible phenotypic trait such as seed color (i.e. yellow, purple or white genes) or shape (i.e. shrunken or plump genes). Selectable markers include genes that provide antibiotic resistance or herbicide resistance. Cells containing selectable marker genes are capable of surviving in the presence of antibiotic or herbicide concentrations that kill untransformed cells. Examples of selectable marker genes include the bar gene which provides resistance to the herbicide Basta, the nptII gene which confers kanamycin resistance and the hpt gene which confers hygromycin resistance. An entire plant can be generated from a single transformed plant cell through cell culturing techniques known to those skilled in the art.

Plants transformed with the DNA constructs of the present invention express the pathogen related gene under the control of a pathogen-inducible regulatory element. Advantageous, the disease resistance gene is expressed at a low basal level, but the products accumulate to a very high level following pathogen induction. Thus, plants carrying the gene constructs of the present invention are less likely to suffer a yield reduction than plants that continuously produce the gene resistant proteins. In addition, it is anticipated that the high level expression directed by the promoter of PR-10a following pathogen attack exceeds that of a constitutive promoter, especially near the site of infection where the protective action of the disease resistant proteins (for example an anti-fungal protein) is most critical.

The protection of rice cultivators from plant diseases is a major challenge to rice farming worldwide. Significant yield losses due to fungal pathogens such as *Magnaporthe grisea* (causal agent of rice blast) and *Rhizoctonia solani* (causal agent of sheath blight) limits crop productivity and can be severe in local epidemic infections. Rice varieties resistant to specific races of certain fungal pathogens have been developed by incorporating one to a few major resistance (R) genes. These cultivators, however, have often failed to remain resistant for even a few years of production.

The production of rice varieties having durable resistance, through the incorporation of multigenic breeding traits, is difficult, but has met with some success. However, although these varieties have durable resistance, the plants remain partially susceptible to disease. For example, rice cultivators IR36, IR24, and Moroberekan have remained more resistant to *M. grisea* infection than many other improved cultivators due to the incorporation of polygenic traits against the disease. Although beneficial, this partial resistance has also proven to be insufficient under heavy infection conditions, and rice blast disease still remains a problem for these varieties.

In accordance with one embodiment a *M. grisea*-induced promoter can be used to drive PR-genes in an attempt to suppress *M. grisea*-induced blast disease, and other pathogens, of rice. This promoter can also be used to drive the expression of other genes of interest wherein it is desirable to express the gene temporally (i.e. in the presence of a detected pathogen) or locally (i.e. localized to a site of pathogenic attack). A substantially purified nucleic acid sequence has isolated for three genes, designated PR-10a, PR-10b, and PR-10c. The promoters of these three PR-10 genes can be utilized to express various disease resistance genes.

EXAMPLE 1

Transformation of Rice Cells

*Agrobacterium tumefaciens* strain, LBA 4404, harboring the binary vector pTOK233 which contains the virB, virC, and virG genes from Ti-plasmid pTiBo542 [as described in Hiei et al. The Plant Journal 6:271–282 (1994)], and within the T-DNA, the npt, hpt, and intron-gusA genes. LBA 4404 (pTOK233) was tested for its potential to produce stably transformed rice callus and plants. Japonica and indica varieties of rice were transformed. Young embryos were co-cultivated with LBA 4404 (pTOK233) for 3 days in the dark at 26° C. and grown for three weeks in 250 mg/l carbenicillin and 100 mg/l cefotaxime. The resulting calli were cut into 1–2 mm sizes and plated for selection with antibiotics (three weeks in 250 mg/l carbenicillin, 100 mg/l cefotaxime and 30 mg/l hygromycin). Plants were then regenerated from the selected calli and grown as putative transgenic plants.

The efficiencies for producing transgenic plants using Agrobacterium-mediated transformation of different varieties of rice are shown in Table 1 (Y.E.=young embryos; $G^+$=Gus positive). For Radon, a japonica variety, the efficiency [see column labeled—No. of Y.E. with $G^+$ plants/embryo plated(%)] averaged about 27%, i.e. 27% of the initial embryos treated yielded transformed plants based upon resistance to hygromycin and expression of GUS activity. Transformation of the putative transformants was confirmed by Southern analysis. All confirmed transformants obtained to date have been fertile with seed-set being nearly equivalent to that obtained from seed-grown plants.

As in the case of Agrobacterium-mediated transformation of dicots, the transgene integration pattern into the rice genome is presumably random, but the number of copies inserted and the frequencies of gene rearrangements are less than that observed by direct DNA uptake methods. Preliminary segregation studies follow a 3:1 segregation ratio for GUS indicating Mendelian inheritance of a single gene. These latter results also eliminate the possibility of Agrobacterium contaminants (or inhabitants) being responsible for the results.

TABLE 1

| | | No. of young embryos | | | | | No. Y.E. with G | | No. Y.E. with G |
|---|---|---|---|---|---|---|---|---|---|
| | | plated | | No. of calli | | | calli | % eff. | plants/embryo |
| Variety | Expt. no. | (A) | with calli | plated | selected | foreign | (B) | (B/A) | plated (%) |
| Radon | 1 | 62 | 42 | 352 | 102 | 45 | 20 | 32.25 | 18/62 (29.0) |
| | 2 | 70 | 62 | 363 | 189 | 101 | 43 | 61.40 | 24/70 (34.3) |
| | 3 | 75 | 53 | 387 | 113 | 68 | 24 | 32.00 | 22/75 (29.3) |
| | 4 | 35 | 34 | 300 | 161 | 104 | 14 | 40.00 | 7/35 (20.0) |
| | 5 | 28 | 14 | 86 | 28 | 13 | 7 | 25.00 | 2/28 (7.1) |
| TSC10 | 1 | 203 | 119 | 987 | 161 | 15 | 13 | 6.00 | 1/203 (0.5) |
| | 2 | 84 | 63 | 384 | 135 | 98 | 5 | 5.90 | 1/84 (1.6) |
| IR72 | 1 | 60 | 48 | 232 | 70 | 52 | 4 | 6.60 | 5/60 (8.3) |
| | 2 | 105 | 53 | 257 | 93 | 51 | 9 | 8.50 | 2/105 (1.9) |

EXAMPLE 2

Isolation of Pathogen Induced Genes

Two cDNA clones were obtained that were induced in Co39 rice seedlings within 72 hours after inoculation with *M. grisea*. These transcripts were not present in uninfected leaves or the fungus, and were obtained during a search for genes that were induced during the *M. grisea* infection process. These rice clones are designated as MAG-6 and MAG-7.

Southern hybridization of Co39, IR36, and IR54 genomic DNA to MAG-6 and MAG-7 probes indicated that there are at least two copies of the gene in each haploid genome. Southern and nucleotide sequence analyses revealed that MAG-6 and MAG-7 are truncated cDNAs derived from the same gene and are 343 bp and 537 bp, respectively.

A full-length (813 bp) cDNA corresponding to both the MAG-6 and MAG-7 cDNAs was made using reverse transcription-polymerase chain reaction (RT-PCR) methodologies with poly (A) RNA isolated from Co39 seedlings 72 hours after inoculation with *M. grisea*. Sequence analyses of this cDNA revealed a 474 bp open reading frame (ORF). This ORF shares sequence homology with a known class of PR proteins found in a variety of plants, including parsley and potato which have been categorized as PR-10 proteins by the system of van Loon et al. Plant Mol. Biol. Rep. 12:245–264 (1994). Although the function of PR-10 proteins is unclear, a recently isolated PR-10 protein has been reported to have RNase-like activity.

A Northern blot of total RNA using radiolabeled MAG-7 cDNA identified transcripts which were expressed at low levels at zero time, but were induced markedly in rice leaf tissue within 12 hours of *M. grisea* inoculation. This mRNA accumulation increased further at 48, 72, and 144 hours after inoculation. These results confirmed that *M. grisea* enhances the production of specific mRNAs, and that this induction occurred quite quickly and resulted in a large accumulation of transcript.

A Co39 genomic library was screened using the 537 bp insert taken from the original MAG-7 cDNA clone. One plaque which hybridized to this probe was found to contain three genes (named PR-10a, PR-10b and PR-10c) all sharing homology to the MAG-7 cDNA. PR-10a (SEQ ID NO: 1) has been sequenced in its entirety including ca. 1.5 kb of the 5' promoter region. This gene shares 100% sequence homology to the MAG-7 cDNA made by RT-PCR. The remaining two genes, PR-10b (SEQ ID NO: 2) and PR-10c (SEQ ID NO: 3), have also been sequenced. PR-10b (SEQ ID NO: 2) comprises approximately 272 bp of the 5' promoter region and approximately 329 bp of 5' coding region.

EXAMPLE 3

Characterization of the PR-10 Gene Expression

To observe the transcriptional differences of the three PR-10 genes, gene-specific probes were constructed representing either the 5' or 3' untranslated regions of the respective genes. Total RNA was isolated from Co39 seedling leaves at 0, 12, 18, 24, 36, 48, 72, and 144 hours after infection with *M. grisea* and was subjected to Northern blot analysis using the PR-10 gene specific probes. The Northern blot analysis for the PR-10a gene indicated that gens transcription was induced within 12 hours of inoculation, and that the PR-10a gene transcript accumulated from a low basal level to increasing levels through 144 hours post inoculation. The detectable number of transcripts for the PR-10b gene also increased after inoculation by *M. grisea*. The induced expression of PR-10b appeared later than rice PR-10a and was first strongly visible at 48 hours post inoculation. Induced expression of the PR-10c gene was not detected after inoculation by *M. grisea* throughout the 144 hour time period.

To identify the tissues expressing the PR-10a gene in relation to the site of pathogen infection, tissue prints of *M. grisea* infected Co39 leaves were made using the gene-specific probe for the PR-10a gene. Two-week old seedlings were inoculated with 20 μl drops of *M. grisea* conidia (0.4% gelatin, 50 conidia/μl), incubated for 72 hours, pressed onto nylon membranes, and hybridized to the PR-10a probe. Hybridization of the PR-10a probe was found to occur only at the site of infection and illustrates that the PR-10a transcript is induced in a localized fashion by *M. grisea*.

In accordance with the present invention PR-genes can be introduced into plants under the control of the *M. grisea*-induced promoters, PR-10a, PR-10b or PR-10c. We anticipate the use of such a pathogen-induced promoter to drive PR-genes will be more effective in decreasing disease severity, than the constitutive expression of the PR-genes.

We claim:

1. A plant expression vector comprising a pathogen-inducible regulatory element selected from the sequence set forth in SEQ ID NO: 1, SEQ ID NO: 2, or SEQ ID NO: 3, and a core promoter.

2. The plant expression vector of claim 1 further comprising a pathogen related gene operably linked to the core promoter, wherein the expression of the pathogen related gene is regulated by the pathogen-inducible regulatory element.

3. The expression vector of claim 1, further comprising a selectable marker gene.

4. The expression vector of claim 1, wherein the pathogen-inducible regulatory element comprises the regulatory element of SEQ ID NO: 1.

5. A polynucleotide sequence having a 20 base pair nucleotide portion identical in sequence to a consecutive 20 base pair portion of the sequence as set forth in SEQ ID NO: 1 or SEQ ID NO: 2.

6. A plant entity consisting essentially of a plant cell, seed or plant produced from the in vitro introduction of exogenous nucleic acid sequences into a plant cell, said exogenous nucleic acid sequences comprising a pathogen related gene operably linked to a pathogen-inducible promoter selected from the sequence set forth in SEQ ID NO: 1, SEQ ID NO: 2, or SEQ ID NO: 3.

7. The plant entity of claim 6, wherein the promoter comprises the regulatory elements of SEQ ID NO: 1.

* * * * *